(12) United States Patent
Reichardt et al.

(10) Patent No.: US 9,345,802 B2
(45) Date of Patent: May 24, 2016

(54) ABSORBENT ARTICLE WITH BARRIER COMPONENT

(75) Inventors: Nicole Anja Reichardt, Sulzbach am Taunus (DE); Christian Springob, Lorsch (DE); Brian Udengaard, Lystrup (DK); Lone Kondrup Hummelgaard, Aalborg (DK)

(73) Assignee: The Procter & Gamble Company, Cincinnati, OH (US)

( * ) Notice: Subject to any disclaimer, the term of this patent is extended or adjusted under 35 U.S.C. 154(b) by 956 days.

(21) Appl. No.: 13/324,089

(22) Filed: Dec. 13, 2011

(65) Prior Publication Data

US 2012/0109090 A1 May 3, 2012

Related U.S. Application Data

(63) Continuation of application No. PCT/US2010/037213, filed on Jun. 3, 2010.

(30) Foreign Application Priority Data

Jun. 25, 2009 (EP) ..................................... 09163722

(51) Int. Cl.
| | | |
|---|---|---|
| *A61F 13/514* | (2006.01) | |
| *A61L 15/34* | (2006.01) | |
| *A61F 13/494* | (2006.01) | |
| *A61L 15/24* | (2006.01) | |

(52) U.S. Cl.
CPC .............. *A61L 15/34* (2013.01); *A61F 13/494* (2013.01); *A61F 13/51405* (2013.01); *A61L 15/24* (2013.01)

(58) Field of Classification Search
CPC ..... A61F 13/15; A61F 13/49; A61F 13/4965; A61F 13/496; A61F 13/51; A61F 13/514; A61F 13/56; A61K 9/145; A61L 15/20; A61L 15/42; A61L 15/46; A61Q 19/00
USPC ........... 604/385.22, 385.24–385.27; 424/402, 424/443, 444, 484, 502; 428/519; 442/327, 442/394, 400
See application file for complete search history.

(56) References Cited

U.S. PATENT DOCUMENTS

| | | | | |
|---|---|---|---|---|
| 4,443,513 | A | * 4/1984 | Meitner | .................... B32B 5/26 264/288.8 |
| 4,578,414 | A | * 3/1986 | Sawyer | .................. C08K 5/103 523/169 |
| 5,607,760 | A | 3/1997 | Roe | |
| 5,609,587 | A | 3/1997 | Roe | |
| 5,635,191 | A | 6/1997 | Roe et al. | |
| 5,643,588 | A | 7/1997 | Roe et al. | |
| 5,690,949 | A | * 11/1997 | Weimer et al. | ................. 424/402 |
| 2004/0058609 | A1 * | 3/2004 | Bansal et al. | .................. 442/400 |
| 2004/0197554 | A1 | 10/2004 | Bond et al. | |
| 2007/0254176 | A1 * | 11/2007 | Patel et al. | ..................... 428/519 |
| 2007/0275622 | A1 * | 11/2007 | Masuda et al. | ................. 442/327 |
| 2008/0108268 | A1 * | 5/2008 | Little et al. | ..................... 442/394 |
| 2008/0287896 | A1 * | 11/2008 | Vega et al. | .................... 604/364 |

FOREIGN PATENT DOCUMENTS

| | | |
|---|---|---|
| EP | 1417945 | 5/2004 |
| EP | 1992366 | 11/2008 |
| WO | WO 95/24173 | 9/1995 |
| WO | WO 2005/112854 A | 12/2005 |

OTHER PUBLICATIONS

Lyondell Basell Industries Holdings, Product Info for PP 8150 polybutylene copolymer, https://polymers.lyondellbasell.com/portal/binary/com.vignette.vps.basell.productgrade.ProductGradeFileDisplay?id=903dc75de41fd010VgnVCM100000646f3c14RCRD&type=iso.*
International Search Report and Written Opinion, PCT/US2010/037213, date of mailing Oct. 12, 2010.

* cited by examiner

*Primary Examiner* — Melanie Hand
(74) *Attorney, Agent, or Firm* — Christian M. Best

(57) ABSTRACT

An absorbent hygiene article that comprises a barrier component, which comprises a nonwoven barrier sheet, comprising at least a spunbond nonwoven web or layer with spunbond fibers and/or a meltblown nonwoven web or layer with meltblown fibers, either or both or all layers comprising fibers comprising thermoplastic polymers and an organic additive component.

29 Claims, No Drawings

ABSORBENT ARTICLE WITH BARRIER COMPONENT

CROSS REFERENCE TO RELATED APPLICATION

This application is a continuation of International Application PCT/US/2010/037213, with an international filing date of Jun. 3, 2010, which claims foreign priority benefits under 35 U.S.C. §119(a)-(d) of EP Patent Application No. 09163722.3, filed Jun. 25, 2009, which are herein incorporated by reference.

FIELD OF THE INVENTION

This invention is directed to an absorbent hygiene article comprising a barrier component. The absorbent hygiene article may comprise an absorbent core and a core coversheet, said barrier component comprising a nonwoven barrier sheet, the nonwoven barrier sheet comprising at least one nonwoven layer or web of fibers made of thermoplastic polyolefin polymers and a specific organic additive component. The organic additive component may improve the barrier properties of the barrier sheet and component, and may improve its comfort (e.g., reduce its stiffness).

BACKGROUND OF THE INVENTION

It is well known in the art to provide absorbent hygiene articles such as sanitary napkins and diapers with a liquid barrier component, such as side flaps, leg cuffs, barrier cuffs, or for example with an anal and/or genital cuff, also referred to as a topsheet with one or more openings. These cuffs have a high barrier function, to stop bodily exudates from wetting the skin, or from leaking out of the absorbent article.

This is for example described in co-pending application EP-A-1417945, which describes hydrophobic topsheets with one or more openings, which have a high alcohol repellency, in order to provide no (re)wetting of the skin by any bodily exudates stored under the topsheet.

It has been found that often materials that provide a good barrier are not very comfortable in use, because these materials may be too thick or too stiff. It may be desirable that the barrier components are made of materials that not only provide an excellent barrier for urine, faeces or blood, but that the barrier components are also very soft and flexible for the sensitive (baby) skin, and that they are easy to fold and easy to elasticise, forming comfortable folds or wrinkles.

Thus, there is a need for further improved barrier components for absorbent articles that are not only an excellent barrier but also comfortable in use, even when folded or wrinkled.

SUMMARY OF THE INVENTION

A solution has been found to provide an absorbent hygiene article with a comfortable and soft barrier material, comprising one or more nonwoven layers or webs, made of thermoplastic polymers fibers and a specific additive component, that surprisingly has been found to impart a low intrinsic surface energy to the thermoplastic polymer fibers. Consequently, the barrier materials made of these fibers comprising the additive component have an improved low surface tension liquid strike through, e.g., an excellent liquid-impermeability.

The present invention relates to an absorbent hygiene article comprising a barrier component, which comprises a nonwoven barrier sheet, comprising a nonwoven web or nonwoven layer made of fibers, obtainable from a mixture of one or more thermoplastic polymers and an additive component comprising one or more fatty acid esters, as described herein below in detail.

In some embodiments, the additive component comprises at least a triglyceride.

It has been found that the addition of the melt additive component to the thermoplastic polymers, e.g. prior to formation of the fibers and of formation of the fibers into a nonwoven web or layer, may make the nonwoven barrier material/barrier component less stiff and thereby softer and more comfortable, and easier to elasticate, whilst providing at the same time excellent liquid-impermeability to said barrier component, even when the component or sheet is stretched or has been stretched. Thus, the absorbent articles comprising said barrier component may have an excellent performance whilst being soft and comfortable to wear and whilst easily further elasticated.

In one embodiment, at least the surface area of the barrier component that in use would be in touch with, or facing, the skin of the wearer comprises a nonwoven barrier web or layer of fibers made by polyolefin polymers and an organic additive, as described herein. In one embodiment, the barrier material comprises at least a spunbond layer or web with spunbond fibers with said additive component.

The nonwoven web comprising said fibers described herein may be, for example, a spunmelt web, comprising spunbond and melt-blown layers, whereof at least one comprises fibers, made of said additive component and said polyolefin polymers, for example, polypropylene.

The additive component may be added as a melt, i.e., being a melt additive component, to said thermoplastic (polyolefin) polymers, prior to fiber formation. In one embodiment, the melt additive component comprises one or more fatty acid esters. In some embodiments, the additive component is a fatty acid ester of alcohols with two or more hydroxyl groups, that are formed into ester bonds with fatty acids (same or different ones).

Said nonwoven barrier sheet may comprise a spunmelt nonwoven SMMS web with a Low Surface Tension Strike Through value of at least 20 seconds, or a spunmelt nonwoven SMMMS web with a Low Surface Tension Strike Through value of at least 40 seconds.

The barrier component may be a side panel (including side flap, front ear, back ear, fastener, or so-called wing), or backsheet, or in one embodiment, a cuff of said article. The barrier component may comprise a skin care composition (lotion) and/or an ink composition. It may comprise an additional elastic material, for example in the form of an elastic film layer, band or strand.

Said nonwoven barrier sheet may have pores of a maximum pore size of less than 60 microns, or less than 50 microns, as determined by the method set out herein. The pores may be of mean flow pore size of from 1 to 30 microns, or from 5 to 20 microns. The barrier component may have also have a maximum pore size and mean flow pore size within the same range as above.

DETAILED DESCRIPTION OF THE INVENTION

As used herein, the following terms have the following meanings:

As used herein, 'absorbent article' means any article that can absorb body fluids and is suitable to be placed in close proximity to the genitals and/or anus of the user, including in particular sanitary pads or napkins, panty-liners, or adult incontinence pads; adult incontinent briefs; adult diapers; and baby, infant or toddler diapers, including so-called training pants.

As used herein 'front region' and 'back region' refer to the two regions, which are in use, respectively, closest to the front of the wearer and the back of the wearer.

When used herein, 'longitudinal' is the direction running substantially parallel to the maximum linear dimension of the component or article, and includes directions within 30° of this parallel, when applicable.

The 'lateral' or 'transverse' direction is perpendicular to said longitudinal direction and in the same plan of the majority of the article and the longitudinal axis, and includes directions within 30° of this parallel, when applicable.

As used herein, 'elasticated' means that the barrier component comprises an additional elastic material, which is elastic in at least one direction, present in addition to the nonwoven barrier sheet.

As used herein, 'along' means 'at least partially substantially parallel to and adjacent to'. Adjacent includes 'in close proximity with' and 'in contact with'.

As used herein, the term "meltblown fibers", refers to fibers formed by extruding a molten thermoplastic (polymeric) material through a plurality of fine, usually circular, die capillaries as molten threads or filaments into a high velocity gas (e.g., air) stream which attenuates the filaments of molten thermoplastic (polymeric) material to reduce their diameter to the required diameter. Thereafter, the meltblown fibers are carried by the high velocity gas stream and are deposited on a collecting surface to form a web or layer of randomly dispersed meltblown fibers.

As used herein, the term "spunbonded fibers" refers to fibers that are formed by extruding a molten (polymeric) thermoplastic material as filaments from a plurality of fine, usually circular, capillaries of a spinneret with the diameter of the extruded filaments then being rapidly reduced by drawing. A spunbond nonwoven layer or web may be produced, for example, by the conventional spunbond process wherein molten polymer is extruded into continuous filaments which are subsequently quenched, attenuated by a high velocity fluid, and collected in random arrangement on a collecting surface. After filament collection, any thermal, chemical or mechanical bonding treatment, or any combination thereof, may be used to form a bonded web or layer such that a coherent structure results.

The nonwoven barrier component or nonwoven barrier sheet or nonwoven webs herein have the values such as number average fiber diameter, largest pore size, mean flow pore size, average fiber denier, hydro head, strike through as used herein, when said component, sheet or web has such a value on at least part thereof, as defined in the test methods set out herein, or, in some embodiments, at least 50% of the component, sheet or web; in some embodiments, said component, sheet or web has said values over the whole component, sheet or web, where applicable.

Nonwoven Component and Nonwoven Barrier Sheet

The barrier component herein comprises a nonwoven barrier sheet, and, optionally, additional materials that may be not nonwoven materials, such as a sheet material that is not a nonwoven sheet, but, for example, a thermoplastic film, and/or an elastic material that may be in the form of an elastic film, or in the form of an elastic strand or band, as further described herein. The barrier component may also comprise further additional materials, such as a lotion (or skin care composition) and/or an ink composition.

The nonwoven barrier sheet may comprise a single nonwoven web or a multitude of (i.e. at least two, or, for example, two) nonwoven webs. A "nonwoven web" as used herein is a web material that is capable of being transferred from its production point to then be incorporated in or formed into said nonwoven barrier sheet herein. A nonwoven web herein includes: 1) nonwoven webs that comprise a single nonwoven; 2) nonwoven webs that comprise two or more nonwoven layers formed on one another (and not being individually transferable) during web formation before bonding (such as spunmelt webs, described below); and 3) laminated nonwoven webs, formed by laminating nonwoven webs to one another after individual web formation (also referred to herein as nonwoven laminate webs); 4) and combinations of 2) and 3).

The nonwoven barrier sheet may comprise two or more of such nonwoven webs, which may be partially attached to one another (but not laminated), as described herein below and/or which may be partially separated from one another by an additional material that is not a nonwoven web.

The nonwoven barrier sheet comprises at least one nonwoven web or nonwoven layer, obtainable from a thermoplastic polymer or mixture of thermoplastic polymers, and an additive component, which comprises one or more fatty acid esters, described below.

The fibers are made of thermoplastic polymers, including polymer compositions, mixtures and blends. Examples of suitable thermoplastic polymers for use herein include polyolefins such as polypropylene, polyethylene, or polyethylene-polypropylene copolymers; polyesters; polyamides; polyhydroxyalkanoates; and mixtures thereof. Other suitable thermoplastic polymers include biodegradable polymers such as PHAs, PLAs, and starch compositions.

The fibers herein may also be multicomponent fibers, including bicomponent fibers; a bicomponent fiber may be in a side-by-side, sheath-core, segmented pie, ribbon, or islands-in-the-sea configuration. The sheath may be continuous or non-continuous around the core. The sheath may comprise polypropylene.

In one embodiment, the fibers comprise polypropylene or polypropylene compositions, including homopolymers of propylene, copolymers of propylene, such as, for example, block, graft, random and alternating copolymers, terpolymers, etc., and blends and modifications thereof. Polypropylene homopolymers, and copolymers of propylene with ethylene and/or butane may be suitably used.

The following are suitable thermoplastic polymers and their surface energy values.

TABLE 1

| Polymer type | Surface Energy |
| --- | --- |
| Isotactic polypropylene | 29.4 mJ/m$^2$ (20° C.) |
| Atactic polypropylene | 29.4 mJ/m$^2$ (20° C.) |
| Mixture of isotactic and atactic polypropylene | 30.1 mJ/m$^2$ (20° C.) |
| Linear polyethylene ($M_w$ = 67000) | 35.7 mJ/m$^2$ (20° C.) |
| Branched polyethylene ($M_n$ = 7000) | 35.3 mJ/m$^2$ (20° C.) |
| Branched polyethylene ($M_n$ = 2000) | 33.3 mJ/m$^2$ (20° C.) |
| Poly(ethylene terephthalate) ($M_n$ = 16000, $M_w$ = 37000) | 44.6 mJ/m$^2$ (20° C.) |

Source: Brandrup, Immergut, Grulke (Editors), Polymer Handbook 4$^{th}$ edition, Wiley-Interscience, New York, 1999.

In one embodiment, the thermoplastic polymers mixed with the additive component are polymers that are not elastic, e.g., non-elastomeric polymers.

One exemplary polymer material is a polymer, e.g. polypropylene polymer, linked with the help of a metallocene catalyst. Such metallocene-polypropylene polymers offer a much greater level of control than conventional polypropylene materials that are connected with the help of a Ziegler-Natta catalyst, because the metallocene molecules offer better control towards how the monomers are linked, so that a proper choice of catalysts can produce isotactic, syndiotactic or atactic polypropylene, or even a combination of these. Further still, they can also produce polypropylene materials with a much narrower molecular weight distribution than traditional Ziegler-Natta catalysts, which can further improve properties, especially in that the narrower molecular weight distribution allows a higher draw ratio, thus allowing thinner fibers to be spun. In one embodiment, the polymer, such as the polypropylene polymer, is isotactic.

The additive component suitably used herein comprises a fatty acid derivative, such as a fatty acid ester; such as an ester formed from an alcohol with two or more hydroxyl groups and one or more fatty acids having at least 8 carbon atoms, or at least 12 carbon atoms, or at least 14 carbon atoms, wherein within one ester compound, different fatty acid-derived groups may be present (herein referred to as fatty acid ester).

The fatty acid ester compound may be an ester of an alcohol carrying two or more, or three or more, functional hydroxyl groups per alcohol molecule, whereby all of said hydroxyl groups form an ester bond with fatty acids (either the fatty acid or mixtures thereof).

In one embodiment, the alcohol has three functional hydroxyl groups.

In one embodiment herein, the additive component comprises a mono- and/or di-glyceride ester, and/or a triglyceride ester, (with one, two or three fatty acid-derived groups).

The fatty acids suitably used herein to form the ester compounds may include fatty acid derivatives. A mono-fatty acid ester, or mono-glyceride, comprises a single fatty acid connected to a glycerol; a di-fatty acid ester, or di-glyceride, comprises two fatty acids connected to a glycerol; a tri-fatty acid ester, or tri-glyceride, comprises three fatty acids connected to a glycerol. In one embodiment herein, the additive component comprises at least a triglyceride ester of fatty acids (the same or different fatty acids).

It should be understood that the triglyceride ester may have an esterified glycerol backbone having no non-hydrogen substituents on the glycerol backbone; however, the glycerol backbone may comprise other substituents. The glycerol backbone of the glycerol ester may comprise only hydrogen. The glyceride esters herein include also polymerized glyceride esters, such as polymerized tri-glyceride esters or polymerized, saturated glyceride esters.

In a fatty acid ester having more than one ester bond, such as in di- or tri-glycerides, the fatty acid-derived group may be the same, or they may be two or even three different fatty acids-derived groups.

The additive component may comprise a mixture of mono-, di-, and/or tri-fatty acid esters (e.g., mono-, di-, and/or triglyceride) esters with the same fatty-acid derived group per molecule, and/or with different fatty acid-derived groups.

The fatty acids may originate from vegetable, animal, and/or synthetic sources. Exemplary fatty acids may range from a $C_8$ fatty acid to a $C_{30}$ fatty acid, or from $C_{12}$ fatty acid to a $C_{22}$ fatty acid.

Suitable vegetable fatty acids may include unsaturated fatty acids such as oleic acid, palmitic acid, linoleic acid, and linolenic acid. The fatty acid may be selected from the group comprising arachidec, stearic, palmitic, myristic, myristoleic, oleic, limoleic, linolenic and arachidonic acid.

In another embodiment, a substantially saturated fatty acid is used, particularly when saturation arises as a result of hydrogenation of fatty acid precursor. In one embodiment, a $C_{18}$ fatty acid, or octadecanoic acid, or more commonly called stearic acid, may be used to form an ester bond of the fatty acid ester herein; stearic acid may be derived from animal fat and oils as well as some vegetable oils. The stearic acid may also be prepared by hydrogenation of vegetable oils, such as cottonseed oil. The fatty acid ester herein may comprise fatty acids of mixed hydrogenated vegetable oil, such as one having CAS registration number 68334-28-1

At least one stearic acid, or at least two, or 3 stearic acid molecules may be connected to a glycerol, to form a glycerol tri-stearate, for the additive component herein. The additive component may comprise at least glycerol tristearate.

In one embodiment, the additive component comprises a glycerol tristearate (CAS No 555-43-1), also known by such names as tristearin or 1,2,3-Trioctadecanoylglycerol. (In the following the name glycerol tristearate will be used, and in case of doubt the CAS No shall be seen as the primary identifier).

In one embodiment herein, the fatty acid ester of the additive component has a number-averaged molecular weight ranging from 500 to 2000, or from 650 to 1200, or from 750 to 1000.

The additive component may comprise very little or no halogen atoms; for example it may comprise less than 5 wt. % halogen atoms (per weight of the additive component), or less than 1 wt. %, or less than 0.1 wt. % of the additive component. The additive component may be substantially halogen-free.

In some embodiments herein the barrier component may comprise less than 1% wt of halogen atoms, or less than 0.5% by weight of halogen atoms, or the barrier component may be substantially free of halogen atoms.

The additive component may comprise other compounds, in addition to one or more of said fatty acid ester compounds. Such other compounds include anti-oxidants and/or a carrier compound, e.g. carrier polymer, such as a polyolefin polymer. In one embodiment, a polyolefin polymer may be present in the additive component, and said polyolefin may have the same monomer units as a polyolefin used for the nonwoven layer or web comprising said additive component.

However, in one embodiment, the additive component comprises at least 50% by weight, or at least 70% by weight, or even at least 90% by weight of said fatty acid ester compound(s). The resulting nonwoven layers or webs herein may, for example, comprise from 1% w/w to 10% w/w of said additive component.

Surprisingly, the surface energy of the resulting thermoplastic polymer (fibers) may be lowered by the addition of the additive component. Furthermore, the addition of the additive component herein does not adversely effect the fiber formation (e.g., the spinablity of the fibers on a spunmelt line), and may even improve the fiber formation, providing a lubrication effect. The additive component may be used at a concentration of 0.1% or 0.5% up to 10%.

Said nonwoven layer or web is obtainable by combining, e.g. mixing, of said thermoplastic polymers, for example, in molten form, and said additive component, e.g., in liquid form, such as in molten form, and then forming this mixture into fibers by any method known in the art, for example, by spunbonding or meltblowing, so that the resulting fibers are, for example, spunbond fibers or meltblown fibers, respectively.

After fiber formation, the additive component may be present throughout the length and diameter (e.g. from the center to the surface) of the fibers. However, in one embodiment, the additive component is present in a higher concentration at the surface than in the centre of the fibers. In one embodiment, the nonwoven web, or barrier sheet, or barrier component, comprising said fibers is heated by a heat source or radiated, or it is compressed, for example by nip rollers, during or after web formation, (e.g., in order to obtain this concentration gradient). This can be done across the whole width of the nonwoven barrier sheet, or in specific lanes, zones or regions (herein referred to as regions). This can be done by the use of zoned compression rollers with varying diameters and nip gaps or pressures, resulting in pressurized regions, or by use of hot, profiled nip rollers, or infra-red heat sources, or other alternating regions of radiating energy, resulting in heat-treated regions. These deliberate activation steps can be employed during the nonwoven web production, or during the nonwoven barrier sheet production, or during storage or packaged transportation thereof, or during further processing thereof into a barrier component, or during final production of the absorbent article. Thus, in one embodiment, the invention relates to absorbent articles with barrier components comprising a nonwoven barrier sheet, comprising a nonwoven web of fibers, obtainable from a mixture of said thermoplastic polymers and said additive component, wherein the fibers in one region of said web have a higher concentration of additive component on the surface of said fibers than in another region, said region being at least 1 mm$^2$; said concentration difference being, for example, at least 10%, or at least 20% or at least 30%.

The additive component can be applied to the thermoplastic polymer(s) that form the fibers of any or all of the nonwoven web, or of any or all of the layers of the nonwoven web of the barrier component.

In one embodiment, the surface area of the barrier component that in use faces the skin of the wearer, or touches the skin of the wearer, comprises at least said nonwoven layer or web comprising said fibers with said organic additive component. In one embodiment, this layer or web is a spunbond nonwoven layer or web.

In a specific embodiment, the nonwoven barrier material or barrier component comprises at least one spunbound (S) or meltblown (M) layer or web that is made of thermoplastic polymer fibers comprising 90% w/w to 99.9% w/w of said thermoplastic polymer material and 0.1% w/w to 10% w/w of said additive component.

The nonwoven barrier sheet may comprise one or more nonwoven webs or layers made of fibers that do not comprise said additive component. Such nonwoven webs and layers may be made of the thermoplastic polymers above, and with the processes described above.

The fibers of one or more of the webs or layers herein may be nanofibers, with a diameter of less than 1000 nanometers. A layer or web may consist exclusively of nanofibers, or it may be mixed with fibers of a larger diameter.

Alternatively, or in addition, the spunbond web or layer herein may, for example, have spunbond fibers with a number average fiber diameter of, for example, from 6 to 22 microns, or from 10 to 18 microns, or from 10 microns or 11 microns to 15 microns or to 14 microns. This may be measured by the test method set out below.

The meltblown web or layer herein may, for example, have meltblown fibers that have a number average fiber diameter from 1 to 5 microns, or from 1 to 4 microns, or from 1 to 3 microns. This is measured by the test method set out below.

The spunbond web or layer may, for example, have spunbond fibers with an average denier of from 0.5 to 2.5 g/9000 m, or from 0.5 to 2.0 g/9000 m, or from 0.8 to 1.5 g/9000 m, or from 0.8 to 1.2 g/9000 m. In one embodiment, the fibers are polypropylene-comprising fibers. Said meltblown fibers may, for example, have an average fiber denier of from 0.02 g/9000 m to 0.5 g/9000 m, or from 0.03 g/9000 m to 0.3 g/9000 m. The meltblown fibers may be polypropylene-comprising fibers. The denier is obtained by the test method set out below, with results reported in grams, which are understood to be grams per 9000 m.

In one embodiment, the nonwoven web useful herein is a spunmelt web (also referred to as "SMS" web) which is a web with (i.e., consisting of) sequential combination and layering of spunbond and meltblown layers, formed on one another during web formation. For example, at first, one or several layers of spunbond fibers are laid down, then one or several layers of meltblown fibers, and lastly one or several layers of spunbond fibers again, followed by a bonding step.

The nonwoven barrier sheet may comprise a multitude (i.e., at least two) of nonwoven webs, for example, laminated to one another or partially laminated to another. As described above, each nonwoven web may be a single nonwoven material, or it may comprise a multitude of layers, such as the spunmelt webs described herein, that comprise spunbond layer(s) and meltblown layer(s), or it may comprise a multitude of nonwoven webs, laminated to one another, and then the nonwoven web is herein referred to also as a nonwoven laminate web. Such lamination of webs to form a nonwoven laminate web may be done by any method, resulting, for example, in an percentage of attachment of more than 60% of the total surface area (where the webs are overlapping (and in contact with) one another), or at least 65%, or at least 70%, or at least 80%.

The two or more nonwoven webs that may be present in a nonwoven barrier sheet herein may be bonded to one another by any method, excluding complete lamination; they may be partially laminated to one another, e.g., such that the percentage of attachment is less than 60% or 40% or less, but, for example, at least 5%, or at least 10%; or they may be indirectly bonded to one another, by binding the webs to either side of a further layer, that is not a nonwoven web, such as a film layer and/or an elastic material, such as an elastic band or strand; or combinations thereof. This may result in a barrier sheet wherein said two or more nonwoven webs are (partially) separated form one another by another layer that is not a nonwoven material; for example, two neighbouring webs are attached to either side of an additional film or elastic band or strand, and, optionally, partially laminated to one another, where this film or elastic band or strand is not present.

In one embodiment, said partial attachment is such that the attachment area between two neighbouring nonwoven webs is less than 60%, or 40% or less, or 25% or less, or 20% or less (of the total area of overlap area between two neighbouring nonwoven sheets), but may be at least 5%, or at least 10%. In one embodiment, two neighbouring nonwoven webs are attached to one another along the side edges of the overlap area (e.g. along the periphery). The nonwoven webs may comprise areas, e.g., of at least 0.5 cm$^2$, where both nonwoven webs are present but not attached to one another.

Laminates and partial laminates herein may be formed by any number of bonding methods known to those skilled in the art including thermal bonding, adhesive bonding, pressure-fusion bonding, sonic and ultrasonic bonding, or combinations thereof.

It should be understood that extrusion processes known in the art, whereby a first nonwoven layer is cast directly onto a second nonwoven layer or on a nonwoven web, and (while still in a partially molten state) bonds to one side of said second nonwoven layer or nonwoven web is not considered lamination herein, but it is herein considered formation of a nonwoven web with multiple layers, e.g. like the spunmelt webs described herein.

In one embodiment, the nonwoven barrier sheet comprises at least a spunbond nonwoven web, or at least a nonwoven web comprising a spunbond nonwoven layer. It may also comprise at least a meltblown nonwoven web or a nonwoven web comprising at least a nonwoven melt blown layer.

In one embodiment, the nonwoven barrier sheet comprises at least two, or at least three, nonwoven meltblown webs or layers and at least two, or at least three, or even at least four, spunbond webs or layers.

In one embodiment, the barrier sheet comprises one or more, for example, two spunmelt nonwoven webs, made up of at least 2 layers of spunbond fibers, and at least 1 layer of meltblown filaments, for example, between said meltblown layers, (e.g., SSMMS material is herein considered to be of the SMS class of materials), i.e., the nonwoven web is manufactured by spunbound/meltblown layering. The barrier component may comprise at least one, or, for example, two, SMMS or SSMMS or SMMMS spunmelt nonwoven web(s).

The use of the above mentioned polypropylene material is particularly useful for the production of nonwovens employing this technique because it allows thinner fibers to be spun. Separately, or in addition, the additive component may have a lubricating effect in the extruder, which has a positive effect on processing conditions and stability. The highest effect of adding an additive component, for example, an additive component comprising a triglyceride ester as described herein, has been achieved in an SMMS and SSMMS and SMMMS spunmelt nonwoven web, because the allowance for thinner spunbound fibers works in synergy with a second effect, being that three of these thin meltblown fibers are contained in an SMMMS spunmelt (MMM), Employing three meltblown layers allows each of them to run at a lower throughput to obtain the same coverage (grams per $m^2$). Thinner and more meltblown fibers result in a lower pore size of the nonwoven and a higher surface area of the fibers. A low pore size makes it more difficult for a liquid to penetrate the material and, as the additive component blooms to the surface and is active with the surface, a high surface area of the fibers increases the effect of the melt additive component. Overall, higher barrier properties are achievable.

The additive component herein may be present in and on the fibers of all layers and webs, or only in and on the fibers of some of the layers and webs, for example, only the first layer or web, or first two layers of a web, that are in use in contact with or facing the skin of the user. In one embodiment, the barrier component comprises at least one spunmelt nonwoven web comprising the additive component in at least two layers, or at least three layers, and/or in all layers, of said web.

The total weight percentage (by weight of the nonwoven barrier sheet) of the meltblown web(s) or layers, may for example be from 5% to 30%, or from 5% to 20%, or from 5% to 15%; or from 8% to 20%, or from 10% to 20%, or from 10% to 15%, by weight of the nonwoven barrier sheet.

The total weight level of meltblown webs in the nonwoven barrier sheet may for example be 10 $g/m^2$ or less; or 9 $g/m^2$ or less, or 7.0 $g/m^2$ or less, or 6 $g/m^2$ or less, for example, from 0.5 to 10 $g/m^2$, or from 1.0 to 8 $g/m^2$, or from 1.5 to 5 $g/m^2$.

Suitable barrier sheet examples are: a 22 $g/m^2$ SMMMS nonwoven web, partially laminated to another 22 $g/m^2$ SMMMS nonwoven web (wherein, for example, the meltblown level of each web is 5%-10% by weight, as described above; and wherein one or more of the spunbond layers comprises said fibers with additive component described above); or a 17 $g/m^2$ SMMMS nonwoven web partially laminated to another 17 $g/m^2$ SMMS or SMMMS nonwoven web (comprising, for example, 5% to 10% by weight meltblown fibers), as described above, and wherein one or more of the spunbond layers comprises said fibers with an additive component described above; or mixtures of such nonwoven webs above, partially laminated to one another. In either case, additional elastic material may be present, as described below, for example, between said two nonwoven webs or part thereof, typically over part of the surface area of said sheet(s), typically in the form of one or more bands and/or strands, as described below.

The nonwoven barrier sheet and/or barrier component may have pores of a largest pore size of less than 60 microns, or less than 50 microns, or less than 45 microns, but, for example, at least 1 microns or at least 2 microns. The nonwoven barrier sheet and/or barrier component may have pores of a narrow pore size distribution. The nonwoven barrier sheet and/or barrier component may have pores of a mean flow pore size within the range of from 1 to 30 microns, or from 5 to 20 microns. This may be measured by the test method set out below.

The nonwoven barrier sheet may have a basis weight of from 10 $g/m^2$ to 70 $g/m^2$, or to 60 $g/m^2$, or to 50 $g/m^2$, or from 15 $g/m^2$ to 45 $g/m^2$ or, in some embodiments, to 35 $g/m^2$. This can be measured by the method set out below.

In one embodiment, the barrier component and/or nonwoven barrier sheet may have a hydrostatic head value (measured with a 52 mN/m surface tension liquid with the hydrostatic head test set out herein) of at least 20 mbar, or at least 25 mbar, or at least 28 mbar, or at least 30 mbar, or optionally at least 35 mbar, and optionally up to 50 mbar or up to 45 mbar. A nonwoven barrier sheet or barrier component is considered to have the above hydrostatic head values if it has this value at any part of the material, excluding areas comprising elastic material or edges attached to another material: i.e., the measurement is done on a sample that does not comprise elastic material or edges attached to another material. In one embodiment, the nonwoven barrier sheet and/or barrier component has a surface area of at least 2.5 cm×2.5 cm that is free of elastics or edges.

The nonwoven barrier sheet and/or barrier component has in one embodiment a surface tension strike through value, as determined by the method described herein, for a liquid of 32 mN/m surface tension, of at least 30 seconds, or at least 40 seconds. The surface tension strike-through value may be limited optionally to less than 250 seconds, or less than 200 seconds or less than 150 seconds. A nonwoven barrier sheet or barrier component is considered to have the above low surface tension strike through values if it has this value at any part of the material, excluding areas comprising elastic material or edges being attached to other materials.

The barrier component may be any component of an absorbent article intended to fulfil barrier functions, including: a backsheet component, side flap, or cuff; or, for diapers, also including: a side panel, a waistband, or a back ear. An exemplary barrier component is part of or forms a cuff. Said cuff may be a barrier cuff, or a leg cuff, or a genital cuff, or an anal cuff, or a genital and anal cuff, such as described below in more detail. The absorbent article may have a pair of such barrier components, e.g. a pair of back ears, a pair of side flaps or a pair of cuffs.

Elastic Material

The barrier component may comprise, in addition to the nonwoven barrier sheet, an elastic material, which may be an elastic film material, or elastic band, strand or filament, or a multitude of such elastic materials, such as a multitude of bands, strands, or filaments, or combination thereof. The portion of the barrier component where said elastic material is present is herein referred to as the elasticated portion.

The elastic material may be attached to a surface of the nonwoven barrier sheet that in use is not facing the skin, or that is not contacting the skin; and/or it may be attached between two of the nonwoven webs that may be present in the nonwoven barrier sheet, as described above. In the event that the elastic material is an elastic band or strand, it may be attached to the nonwoven barrier sheet and covered with an additional covering strip material, so that the elastic band or strand is not in direct contact with the skin of the user in use.

In one embodiment, the barrier component comprises, for example, an elastic film having more than 50% of the width of the barrier sheet or, for example, the full width of the barrier sheet; or, for example, one or more elastic strands or bands, e.g., having a width that is significantly less than the width of the barrier sheet, and forming elasticated portions that have width that is less than 40%, or less than 30%, or less than 20%, of the width of the barrier sheet, further described below. In one embodiment, said elastic material is only present over a part of the surface area of said barrier component and of said nonwoven barrier sheet, for example, between 1% and 30% of the total surface area (measured over the surface of the barrier component/sheet facing the wearer in use), or from 2% to 20%.

In one embodiment, the barrier sheet may be free of barrier film materials, other than elastic band(s) or strand(s), defined as elasticated portions.

In one embodiment, the elasticated portion of the barrier component (e.g., comprising the nonwoven barrier sheet and elastic material at least) may comprise wrinkles of an average wrinkle height of less than 800 microns, or less than 600 microns. To measure this, the elasticated portion is elongated (stretched) to the length that it has an elongation $\epsilon=0.5$, which is: 1-(contracted length/stretched length); for example, if the contracted length is 10 cm, the laminate portion is stretched to the (partially) stretched length of 20 cm, to be elongated to $\epsilon=0.5$). This elasticated portion is examined by use of PRIMOS and its data acquisition software, following the manufacturer's instruction manual, using a 13×18 mm lens. This will calculate the average wrinkle height of the elasticated portion. (If the elasticated portion has an average width of more than 3 mm, then the measurement above is only done on the inner 70% of the width of the laminate portion, along its full length.)

An elasticated portion of the barrier component herein may be formed from a thin strand or a multitude of thin strands of elastic material and/or, for example, from a single band or a multitude of bands of elastic material, attached to said nonwoven barrier sheet, said bands being at least 2 mm wide, in relaxed state, and said strands being less than 2 mm wide in relaxed state. If a multitude of bands and/or strands are present, the average distance of neighbouring bands or strands is at the most 10 mm, in order to be considered part of a single elasticated portion. A barrier component that is a cuff may comprise an elasticated portion along part or all of the longitudinal free edge of the cuff. The width of the elasticated portion may vary, typically depending on the exact dimensions of barrier component, for example, the elasticated portion may have an average width of about 1 mm to 40 mm, or 2 mm to 30 mm, or 2 mm, or even 3 mm to 20 mm. The elastic materials may have an average thickness (e.g., gauge) of at least 20 microns, or at least 40 microns, or even at least 60 microns, up to, for example, about 300 microns, or even up to 200 microns, or even up to 150 microns.

The elasticated portion(s) may be formed by attaching an elastic material in stretched state or partially stretched state to part of the barrier sheet, for example, to part of a surface of the barrier sheet or to a nonwoven web thereof, and/or attaching the elastic material to said nonwoven barrier sheet with a first surface area of the elastic material and then said nonwoven barrier sheet is subsequently folded, e.g. in a C-fold, over the opposite side of the elastic material, to form the elastic portion.

Patterned Barrier Component or Nonwoven Barrier Sheet

In one embodiment, the barrier component or nonwoven barrier sheet, or part thereof, comprises a 3-dimensional pattern, i.e., the barrier component/sheet has a patterned area; this may be an embossed area, ringrolled area or crimped area. Due to the flexibility of the nonwoven barrier sheet and component, such a pattern can be easily and precisely applied and such a patterned area can easily be obtained. Only part of the surface area of said barrier component/sheet may comprise said pattern. The elasticated portion may comprise such a 3-dimensional pattern, in addition to a wrinkle pattern, formed by contraction of said elastic material. Thus, in one embodiment, the barrier component comprises a wrinkled, patterned elasticated portion.

A wrinkled, patterned elasticated portion of the barrier component, which comprises elastic material, is obtainable by:
 a) obtaining a nonwoven barrier sheet or web (thereof), as described herein;
 b) obtaining an elastic material that is at least partially stretched, having at least an average longitudinal direction of stretch Y;
 c) i) submitting said sheet or said web, or part thereof, to a patterning, pressure-applying step to obtain a patterned nonwoven barrier sheet or web thereof, comprising troughs, and then positioning said at least partially stretched elastic material adjacent said patterned sheet or web, to obtain a combined material; or
  ii) positioning said at least partially stretched elastic material (15) adjacent said nonwoven barrier sheet or web thereof, to obtain a combined material and simultaneously or subsequently submitting the combined material, or part thereof, to a patterning, pressure-applying step to obtain a patterned combined material, comprising a patterned nonwoven barrier sheet or web thereof comprising troughs (16);
 d) simultaneously or subsequent to step c) attach the thus formed troughs or part thereof, of the patterned sheet or layer thereof to said elastic material;
 e) optionally, if in the previous steps a nonwoven web of the nonwoven barrier sheet was attached to the elastic material, then attaching another nonwoven web to said patterned layer of the previous steps;
 f) to thus obtain in step d) or e) a barrier component, comprising a patterned elasticated portion;
 g) and then relaxing this barrier component of step f) to obtain a barrier component comprising a wrinkled, patterned elasticated portion, comprising wrinkles with peaks and valleys, said valleys being formed by both said elastic material and the troughs of said nonwoven barrier sheet or web thereof.

At least 10% of the elasticated portion may comprise said pattern of troughs, at least 30%, or even at least 40%, or even at least 60%, or at least 75%, or at least 90%, or even about 100% of its length.

At least 30% of the width of the elasticated portion may comprise said pattern of troughs or, for example, at least 50%, or even at least 70%, or at least 80%, or at least 90%, or even about 100%. Furthermore, the width of the patterned area may be more than the width of the elastic material, for example, the width of the patterned area may be from 100% to 500% of the average width of the elastic material, or from 105% to 250% or from 110% to 150%.

The number of troughs along the elasticated portion of the barrier component/nonwoven barrier sheet may vary; for example, it may have in contracted state an average of from 5 to 25 troughs per cm, or from 5 to 20 troughs per cm, or from 7 to 15 troughs per cm, typically in the machine direction and direction of stretch Y.

The patterning step may be done by applying (indirectly or directly) a patterning surface of a first tool to the surface of the nonwoven barrier sheet or web thereof. Said surface may not face the elastic material. This tool surface may be a continuous surface, and the tool is, for example, a patterned roll, with raised portions (with a first dimension x, parallel to the axis of the tool). The raised portions may have any shape, for example, studs, or teeth.

The opposite surface of the nonwoven barrier sheet or web thereof, which typically faces the elastic material, is pressurized and may be indirectly contacted by a surface of a second tool to apply a counter pressure to the first tool's surface; this second tool's surface may be non-mating with the first tool's surface; it may be a flat surface. The second surface may also be a continuous second surface such as a surface of a second roll.

The patterning step may apply a pressure that is large enough to ensure patterning of the nonwoven barrier sheet or web thereof and contacting of the thus formed troughs with the elastic material and possibly aiding attachment thereof to the elastic material. The applied pressure may be limited, to avoid attachment of the crests to the elastic material. Suitable pressures may depend on the nonwoven barrier sheet's properties, such as, bending rigidity, thickness, and on the type of elastic material chemistry, and on whether, for example, adhesives are used.

The applied pressure may, for example, be from 10,000 to 100,000 psi (from 70 MPa to 700 MPa), or from 20,000 to 80,000 psi (14 MPa to 560 MPa) or, for example, from 30,000 to 60,000 psi (210 MPa to 42 MPa; all obtainable by calculation).

The average distance between the highest point of the raised portions (in x-y plane) of the first tool and highest point of the surface of the second tool may, for example, be from 0.01 and 1.0 mm, or from 0.025 mm to 0.6 mm or to 0.5 mm or to 0.3 mm or to 0.25 mm.

An exemplary average first, length dimension (Y-direction) of the raised portions may, for example, be from 0.01 mm to 3 mm, or from 0.05 to 2.5 mm or to 2.0 mm, or from 0.1 to 2 mm or to 1.5 mm, or to 1 mm or to 0.5 mm; an exemplary average width dimensions (X-direction) of the teeth or studs may, for example, be from 0.01 mm to 5 mm, or from 0.05 to 3 mm or to 2.5 mm, or from 0.1 to 2 mm or to 1.5 mm, or to 1 mm or to 0.5 mm. The width of the ridges herein may be equal to the width of a trough of the patterned elasticized portion.

In addition to helping the formation of comfortable wrinkles, this patterning process step may help create the organic additive component concentration gradient in the fibers of the nonwoven layer(s)/web(s) of the barrier component, described above.

Ink Composition

In one embodiment, the barrier component comprises a pigment, or, for example, an ink composition, comprising a pigment. Such an ink composition may be applied in a pattern, and/or in the form of figure(s) and/or letter(s), for example, by printing. The ink composition may be an aqueous composition. This can be applied to the nonwoven barrier sheet or barrier component despite the presence of fibers on the surface and despite the barrier nature and possibly hydrophobic nature of these barrier components and nonwoven barrier sheets. The pattern may be any pattern, including geometric patterns such a multitude of stripes, dots, squares, ovals, etc.

The ink composition may comprise an aqueous latex component. This may, for example, comprise an elastomeric polymer, for example a vinyl and/or styrene polymer, including styrene acrylic polymers and derivatives thereof and/or styrene butadiene polymers (rubbers) and derivatives thereof. These polymers include also block polymers and copolymers.

It may comprise a surface tension reducing agent, such as a diol surfactant. Surface tension reducing agents may include dioctyl sodium sulfosuccinate or derivatives thereof, ethoxylated glycols, sorbitan esters and/or acetylenic diol-based surfactants, and mixtures thereof. The acetylenic diol-based surfactants may include alkoxylated (e.g. ethoxylated) acetylenic diols, including acetylenic glycols, and derivatives thereof, including alkyl branched derivatives thereof, e.g., with one or more methyl side-groups. The surfactant may, for example, have an alkoxylation (e.g. ethoxyaltion) degree of 2-50, or 4-10, or 4-8. The ink compositions may, for example, comprise ethoxylated 2,5,8,11 tetramethyl-6 dodecyne 5,8 diols and derivatives thereof.

The ink composition may suitably comprise at least a pigment. The pigment may be present at a level of from 0.5% to 40% by weight of the aqueous composition (prior to application), or, for example, from 1% to 30% by weight. The pigment may be in the form of small particles, having an average particle size of less than 1 micron, or, for example, from 0.01-0.20 micron.

Skin Care Composition

In one embodiment herein the barrier component may comprise a skin care composition, also referred to in the art as lotion or lotion composition.

A portion of, or an entire surface of, the barrier component may comprise on its surface (e.g., may be coated with) a skin care composition. Said barrier component may comprise said skin care composition (or lotion) at least on the elasticated portions, described above, if present. Examples of lotions include those described in U.S. Pat. No. 5,607,760; U.S. Pat. No. 5,609,587; U.S. Pat. No. 5,635,191; U.S. Pat. No. 5,643,588; and WO 95/24173.

A hydrophilic skin care composition may reduce adherence of bodily exudates, such as faeces and blood.

A skin care composition may for example comprise: 1) first component comprising one or more liquid (at 20° C.) compounds selected from the group consisting of liquid polyhydric alcoholic solvents, liquid polyethylene glycol, liquid polypropylene glycol, liquid polyethylene glycol derivatives, liquid polypropylene glycol derivatives; liquid nonionic surfactants with HLB value of at least 10; and liquid fatty acid esters comprising at least one fatty acid unit and at least one (poly)ethylene glycol unit and/or (poly) propylene glycol unit; and 2) a second, solid component (at 20° C.) comprising one or more compounds selected from the group consisting of solid polyethylene glycols, solid polypropylene glycol, solid polyethylene glycol derivatives, solid liquid polypropylene glycol derivatives; solid nonionic surfactants with HLB value of at least 10; and solid fatty compounds selected from the group consisting of solid fatty acids, solid fatty soaps and solid fatty alcohols.

The skin care composition may be essentially non-aqueous. Non aqueous means that the lotion composition comprises water only in minor amounts such as less than 5 wt. %, or even less than 1 wt. %, or even no water.

The skin care compositions may include polyethylene glycols, polypropylene glycols, mono- or di-end capped polyethylene glycols, and mono- or di-end capped polypropylene glycols, or other polyethylene glycol derivatives, or polypropylene glycol derivatives, such as esters and ethers.

Suitable liquid alkylene or ethylene glycol fatty acid esters for skin care compositions herein are, for example, the esters of one or more alkylene glycol units, such as ethylene glycol units, and one or two fatty acids. Suitable compounds may have the general formula $R^1$—$(OCH2CH2)_mO$—$R^2$ where $R^1$ and $R^2$ are hydrogen or fatty acid residues with, e.g., from 6 to 30, or from 8 to 22 carbon atoms, and can be the same or different with the proviso that not both are hydrogen; and m is a number of at least 1. In some embodiments, R1 and R2 are different and m is 1, 2, or 3. Exemplary ethylene glycol esters are known, for example, as diethylene glycol diethylhexanoate/diisononanoate, diethylene glycol diisononanoate, diethylene glycol dilaurate, diethylene glycol dioctanoate/diisononanoate and diethylene glycol distearate. Suitable trade product mixtures containing ethylene glycol esters are, for example, DERMOL MO or DERMOL 489. Suitable esters may include wax esters which are liquid at room temperature (25° C.). They may be derived from natural sources such as jojoba oil, comprising docosenyl eicosenoate, eicosenyl eicosenoate and eicosenyl docosenoate.

Suitable solid nonionic surfactants with an HLB value of at least 10 include solid PEG derived nonionic surfactants, solid polyalkylene glycol fatty alcohol ethers, that may have the general formula $R(OCH2CH2)_nOH$, where R represents an alkyl group or a blend of alkyl groups with, for example, 8 to 30, or 12 to 22 carbon atoms and n is the degree of ethoxylation, e.g., 2 to 200. Suitable PEG derived surfactants include PEG-12 stearate, PEG-100 stearate, for example, available as Tego Acid S 100 P from Evonik/Degussa.

Suitable trade products include also, for example, BRIJ 76, BRIJ 78 and BRIJ 700 (Steareth 100, available from Croda Inc.).

Other surfactants include Ceteraeth-10, Ceteareth-20, and Polysorbate-65. Also used may be Laureth 23.

Exemplary skin care compositions may be such that said first liquid component may comprise a liquid polyethylene glycol and said second component may comprise a solid nonionic surfactant with an HLB value of at least 10, provided that when said solid nonionic surfactant is an alkoxylated (e.g. ethoxylated) fatty alcohol, then the HLB value is at least 13; or said first component may comprise a liquid fatty acid ester comprising at least one fatty acid unit and at least one ethylene glycol unit and said second component may comprise a solid polyethylene glycol; or said first component may comprise a liquid polyethylene glycol and said second compound is a solid fatty compound selected from the group consisting of solid fatty acids, solid fatty soaps and solid fatty alcohols.

Barrier Components and Absorbent Hygiene Articles

The absorbent hygiene article herein may be a sanitary napkin or pad; a panty-liner; an adult incontinent pad, or a brief or diaper; or an infant (baby, toddler) diaper, including diapers with fasteners and training pants.

In one embodiment, the absorbent article has a pair of barrier components, for example, a pair of cuffs, a pair of side panels (such as a pair of back ears, a pair of front ears, a pair of fasteners, a pair of side flaps, a pair of so-called wings), or combinations thereof, any or each comprising or being formed by said barrier component. Each side panel may extend longitudinally along a part of a longitudinal side edge of the backsheet and/or of the absorbent core of the article. The side panels of a pair of side panels may be mirror images of one another in the longitudinal axis of the absorbent article.

A side panel may, for example, extend along at least 5%, or at least 10%, of the total length of the article, and, for example, less than 50%, or less than 40%.

Each cuff may extend longitudinally along a longitudinal side edge of the backsheet and/or of the absorbent core of the article. The cuffs of a pair of cuffs may be mirror images of one another in the longitudinal axis of the absorbent article. The cuff may have a free longitudinal edge that can be positioned out of the X-Y plane (longitudinal/transverse directions) of the article, i.e., in z-direction.

The cuff may have a width of at least 1 cm, or at least 2 cm, or at least 2.5 cm. The cuff may extend along at least 50% of the total length of the article, or at least 60%, or at least 70%.

The cuff may be also be a generally H-shaped cuff, having a unitary shape and having two side cuff portions joined to one another in, for example, the crotch region; or a pair of cuffs may be attached to one another with an additional, transversely extending material, such as a transverse strip, in, for example, the crotch region (e.g., the crotch region being the region having the centre ⅓ of the length of the article, between the back and front region of the article, each being also ⅓ of the length of the article).

In another embodiment, the absorbent article comprises an anal and/or genital cuff, comprising or being formed by said barrier component; such a cuff is hereinafter referred to as a topsheet with one or more openings for the reception of bodily exudates, such as blood, urine or faecal material, whereby said bodily exudates can pass through said opening or openings to a void space under the topsheet. As used herein, 'opening' (as present in the topsheet or anal and/or genital cuff) means an area circumscribed by the topsheet, e.g., by the barrier component, but where the topsheet (barrier component) is not present, and which is large enough to receive bodily exudates, e.g. faecal material, for example, being at least 2 cm long or wide, or having a surface area of at least 2 $cm^2$. As used herein, the term 'void space' is a cavity in the article present in at least the relaxed state, which serves to accept and contain bodily exudates, such as faecal material, for example, having a volume of at least 3 or even 5 $cm^3$ in relaxed state.

The opening(s) may be in the form of a slit opening. The opening(s) may be present in part of the front region of the topsheet (in use towards the front of the user) and in part of the back region. The topsheet may have a slit opening with a longitudinal dimension (length) substantially parallel to the longitudinal axis of the topsheet and of the diaper. It may be beneficial that (in stretched state) the opening (or openings) of the topsheet is (are) configured such that from 20% to 40%, or from 20% to 30% of the length of the opening, or total length of the openings, extends from the transverse axis of the topsheet towards the front edge of the topsheet, and the remaining percentage extends towards the back edge of the topsheet.

The topsheet may have at least two elasticated portions, each along part or all of a longitudinally extending side edge of the opening or openings, said elasticated portions, and, in some embodiments, said side edges, being mirror images of one another in the y-axis of the topsheet or article.

Alternatively, or in addition, the absorbent article may comprise a barrier component that is, or is part of, a waistband of the absorbent article.

The absorbent article may comprise a liquid impervious backsheet, which may comprise or may be the barrier component herein, or the backsheet may comprise other nonwoven material and/or film materials as known in the art. Suitable backsheet materials may comprise breathable material, which permit vapors to escape from the diaper while still preventing exudates from passing through the backsheet. In one embodiment herein, the liquid impervious backsheet comprises a thin plastic film, such as a thermoplastic film, having a thickness of about 0.01 mm to about 0.05 mm.

The absorbent article may comprise an absorbent core. The absorbent core may comprise any absorbent material which is generally compressible, conformable, non-irritating to the wearer's skin, and capable of absorbing and retaining urine, such as comminuted wood pulp; creped cellulose wadding; melt blown polymers, including coform; chemically stiffened, modified or cross-linked cellulosic fibers; absorbent foams; absorbent sponges; super absorbent polymers; absorbent gelling materials; or any other known absorbent material or combinations of materials. The absorbent core may have an absorbent storage layer which comprises more than 80% by weight of the absorbent core content (e.g., excluding core cover, if present) of water-absorbent polymer particles or water-absorbent gelling polymers. The absorbent core or storage layer thereof may be free of absorbent cellulose fibers.

The absorbent core may be covered by a core cover that covers at least the body-facing surface of the core, which may be in close proximity or in contact with the skin of the user. Suitable core coversheets include liquid permeable nonwovens.

The core cover can serve as topsheet of the article, and thus be, during use, in contact with the skin of the user, or an additional topsheet may be present. Such a topsheet may be a nonwoven material and/or an apertured film or an apertured formed film, for example.

The nonwoven webs or layers used as part of the backsheet material or core cover sheet or topsheet may, for example, be webs or layers of natural fibers (e.g., wood or cotton fibers), or synthetic fibers (e.g., polyester or polypropylene or polyethylene or bicomponent fibers), or a combination of natural and synthetic fibers. The fibers may be spunbond, carded, wet-laid, melt blown, hydro entangled, or otherwise processed as is known in the art.

The absorbent article may be a disposable infant diaper with fasteners, also referred to as fastening system, or infant pre-fastened training pants, that may comprise a re-fastening system. The re-fastening system may be joined to or part of the waistband, as known in the art. Fastening systems may comprise fastening tabs and landing zones, wherein the fastening tabs are attached or joined to the back region of the diaper and the landing zones are part of the front region of the diaper.

It should be understood that the absorbent article may alternatively comprise side panel(s), cuff(s), waistband(s), fastening ear(s) that do not comprise the barrier component herein, but other materials known in the art.

Test Methods

Basis Weight:

The basis weight herein can be measured consistent with ASTM D 756, ISO 536 and EDANA ERT-40.3-90. It is defined as mass per unit area, in g/m$^2$ (also referred to as gsm), and measured on the component or sheet as a whole, if possible with this method, or a sample thereof; the total sample surface area may be any size suitable for the test method, but preferably a sample of 100 cm$^2$ (±0.5%) is used. The sample is conditioned at 23° Celsius (±2° C.) and at a relative humidity of 50% for 2 hours to reach equilibrium, prior to weight determination.

Fiber Diameter:

The number average fiber diameters herein are determined by using a Scanning Electron Microscope (SEM) and its image analysis software. A magnification is chosen such that the fibers are suitably enlarged for measurements, e.g., between 1,000 and 10,000. At least 100 fibers are measured, and the number average fiber diameter is calculated with the software and used herein.

Fiber Denier:

In order to determine the average fiber denier, the number average fiber diameter is first obtained by the method above.

Fiber denier=Cross-sectional area(in m$^2$)*density(in kg/m$^3$)*9000 m*1000 g/kg.

The cross-sectional area is $\pi$*diameter$^2$/4. The density of the fibers used is known from suppliers, text books, etc; for example for polypropylene fibers the density is reported to be 910 kg/m$^3$.

Maximum (Largest) Pore Size and Mean Flow Pore Size Determination:

The maximum pore size and mean flow pore size as used herein can be measured with a PMI Porometer in accordance with ASTM E1294-89 and F316-89 methods (capillary Constant as per ASTM method is 1; wetting fluid is Galwick, with Surface Tension of 15.9 mN/m; the surface tension of this fluid can be determined as set out herein below).

As Porometer, a PMI Capillary Flow Porometry, model CFP-1200-AEX, may suitably be used.

A wrinkle free, clean circular sample is obtained from the barrier component (which is free in the sample area of elastic material or film material, as described herein) or nonwoven barrier sheet (depending on which value needs to be tested in accord with the invention), having a diameter of 1.0 cm (conditioned for 2 hours at 20° C., 50% relative humidity). Using tweezers, the sample is immersed in the petri dish filled with the Galwick 15.9 mN/m wetting fluid such that the fluid completely covers the sample, for 30 seconds. Then the sample is turned, using tweezers, and re-immersed in the same dish and fluid, for a further 30 seconds. This ensures complete saturation of the pores with the wetting fluid.

Then, using tweezers, the saturated sample is directly placed onto the O-ring of the lower sample adaptor, without allowing the wetting fluid to drain, ensuring that that the O-ring is completely covered by the sample, but without covering the gauze during placement of the sample.

With the O-ring and sample facing upwards on the lower adopter and facing the upper adaptor, the Porometer is further prepared as per its manual and the measurement is started according to manual. The apparatus' software will analyse the measurements and report the maximum pore size as used herein. It will also calculate the mean flow pore size.

Hydrostatic Head (Hydro Head):

The hydrostatic head (also referred to as hydro head) as used herein is measured with a low surface tension liquid, i.e. a 52 mN/m liquid (solution).

This liquid is prepared as set out below.

This test is performed as set out in co-pending application WO2005/112854A, conform the Inda/Edana test WSP 80.6 (05). However, the water pressure (from below) is increased with a rate is 60 mbar/min.

A sample of 5 cm$^2$ is taken from the barrier component or nonwoven barrier sheet. The sample should be free from elastic material or edges that are connected to other materials.

The test head used has a 2.5 cm diameter; the protective sleeve used has a 2.2 cm diameter.

The test is performed on this sample and the Hydrostatic head value is obtained, and referred to herein.

52 mN/m (dynes/cm) Liquid Preparation:

A 10 liter canister with tap is cleaned thoroughly 3 times with 2 liters polyethylene and then 3 times with 2 liters distilled/deionized water.

Then, it is filled with 10 liters distilled/deionized water and stirred with a clean stirring bar for 2 h, after which the water is released via the tap.

A 5 liter glass is cleaned 6 times with water and then 6 times with distilled/deionized water.

Then, 30.00 g of Na Cholate and 5 liters of distilled/deionized water are placed in the cleaned 5 liters glass. (NaCholate should have a TLC purity of >99%, e.g. supplied by Calbiochem, catalog #229101). This is stirred with a clean stirring bar for about 5 min, until the Na Cholate is visibly dissolved.

The stirring bar is removed from the glass with a magnetic stick (without touching the solution) and then the Na cholate solution is poured into the 10 liters canister and more distilled/deionized water is added such that the concentration of the final solution is 3 g/l. This is further stirred with a stirring bar for 2 hours and then used.

This preparation of the solution and use thereof is at the temperature stated for the test for which it is used, or if no temperature is stated, it is kept at 20° C.

The surface tension of the solution is measured and this should be 52 mN/m. (The surface tension may be determined by method: ASTM D1331-56 ("Standard test method for surface and interfacial tension of solution of surface active agents") using a Kruss K12 tensiometer.)

Low Surface Tension Strike Through (LST. ST) Method

The low surface tension strike through value referred to herein may be obtained by the Edana method WSP70.3 (05), except that a low surface tension liquid (see below) is used and a sample of 1 inch×1 inch (25 mm×25 mm) may be used. The sample should be free of elastic material or of edges that are connected to other materials.

The value obtained from this sample measurement is reported herein.

The low surface tension liquid is a liquid with a surface tension of 32 mN/m prepared as follows:

In a clean flask, 2.100 grams of Triton-X-100 is added to 500 ml distilled water (already in flask) and then 5000 ml distilled water is added. The solution is mixed for 30 minutes and then the surface tension is measured, which should be 32 mN/m.

(The surface tension may be determined by method: ASTM D1331-56 ("Standard test method for surface and interfacial tension of solution of surface active agents") using a Kruss K12 tensiometer.)

Handle-O-Meter Stiffness

The Handle-O-Meter Stiffness was measured according to the standard test method WSP 90.3.0 (05).

Alcohol Repellency

Alcohol Repellency (AR) was measured by INDA IST 80.8. INDA IST 80.8. is a standard test method for measuring the resistance of nonwoven fabrics to penetration by aqueous isopropanol solutions. The alcohol repellency was reported in ratings based upon alcohol concentrations. The highest number of test solutions that did not penetrate the tested fabric within five minutes was recorded.

Comparative Example 1

An SMMMS spunmelt nonwoven web was produced from metallocene-polypropylene in a continuous production on a 4.5 m wide Reifenhäuser Reicofil 4 SMMMS line. Each layer of S-layers had a weight of 9.5 g/m$^2$ and each of the M layers had a weight of 1.0 g/m$^2$, resulting in a thermally bonded SMMMS nonwoven web having a total weight per area of 22 g/m$^2$.

In each of the following Examples, the single layers of the SMMMS sheet will be denoted as indicated in parentheses: S(1)M(2)M(3)M(4)S(5).

Example 1

A spunmelt nonwoven web was produced following the process described in Comparative Example 1, where the polymers forming Layers 2, 3 and 4 contained 2.3% w/w of additive component, comprising at least 90% by weight of the additive component of glycerol tristearate (available under CAS reference number 555-43-1), resulting in an average weight percentage of 0.3% w/w of active ingredient in the total web.

Example 2

A spunmelt nonwoven web was produced as described in Example 1, where the polymers forming each of the Layers 2, 3 and 4 contained 2.3% w/w and the one forming Layer 5 contained 2.0% w/w of the additive component above, resulting in an average weight percentage of 1.2% w/w of active ingredient in the total web.

Example 3

A spunmelt nonwoven web was produced as described in Example 1, where the polymers forming each of the Layers 2, 3 and 4 contained 2.3% w/w, and the one forming Layer 5 contained 3.0% w/w of additive component, as above, resulting in an average weight percentage of 1.6% w/w of active ingredient in the total fabric.

The content of active ingredient of Comparative Example 1 as well as Examples 1, 2 and 3 are summarized in Table 2.

TABLE 2

| | Lay-up [g] | | | | | Configuration |
|---|---|---|---|---|---|---|
| | S | M | M | M | S | SMMMS |
| | 9.5 | 1 | 1 | 1 | 9.5 | 22 g |
| Example | Active ingredient per layer [%] | | | | | Average [%] |
| C1 | 0.0 | 0.0 | 0.0 | 0.0 | 0.0 | 0.0 |
| 1 | 0.0 | 2.3 | 2.3 | 2.3 | 0.0 | 0.3 |
| 2 | 0.0 | 2.3 | 2.3 | 2.3 | 2.0 | 1.2 |
| 3 | 0.0 | 2.3 | 2.3 | 2.3 | 3.0 | 1.6 |

The following tests were carried out according to the method introduced in the section "Test Methods" to assess the low surface tension Strike Through (32 mJ/m$^2$) Properties, for Comparative Example 1 as well as Examples 1, 2 and 3 and the results are shown in Table 3.

TABLE 3

| Example | C1 | 1 | 2 | 3 |
|---|---|---|---|---|
| LST Strike through (32 mJ/m$^2$) [s] | 25.59 | 42.42 | 64.57 | 79.17 |
| Increase of LST ST [%] | 0 | 66 | 152 | 209 |

Comparative Example 2

An SMMMS spunmelt nonwoven web was produced from metallocene-polypropylene in a continuous production on a 4.5 m wide Reifenhäuser Reicofil 4 SMMMS line. Each layer of S-layers had a weight of 6.5 g/m$^2$ and each of the M layers had a weight of 1.3 g/m$^2$, resulting in a thermally bonded SMMMS layered nonwoven product having a total weight per area of 17 g/m$^2$.

In each of the following two Examples, the single layers of the SMMMS sheet will be denoted as indicated in parentheses: S(1)M(2)M(3)M(4)S(5).

Example 4

A spunmelt nonwoven web was produced as described in Comparative Example 2, where the polymers forming each of the Layers 2, 3 and 4 contained 2.9% w/w and the one forming Layer 5 contained 3.5% w/w of the additive component (as in examples 1, 2 and 3 above), resulting in an average weight percentage of 2.0% w/w of the additive component in the web.

Example 5

A spunmelt fabric was produced as described in Example 17, where the polymers forming each of the Layers 2, 3 and 4 contained 3.9% w/w, and the one forming Layer 5 contained 4.8% w/w of active ingredient, resulting in an average weight percentage of 2.7% w/w of the additive component in the total web.

The content of the additive component of Comparative Example 2 as well as Examples 4 and 5 are summarized in Table 4.

TABLE 4

| | Lay-up [g] | | | | | Configuration |
|---|---|---|---|---|---|---|
| | S | M | M | M | S | SMMMS |
| | 6.5 | 1.3 | 1.3 | 1.3 | 6.5 | 17 g |
| Example | Active ingredient per layer [%] | | | | | Average [%] |
| C2 | 0.0 | 0.0 | 0.0 | 0.0 | 0.0 | 0.0 |
| 4 | 0.0 | 2.9 | 2.9 | 2.9 | 3.5 | 2.0 |
| 5 | 0.0 | 3.9 | 3.9 | 3.9 | 4.8 | 2.7 |

The Low surface tension Strike Through test was carried as above, resulting the results set out in table 5.

TABLE 5

| Example | C2 | 4 | 5 |
|---|---|---|---|
| Strike through (32 mJ/m$^2$) [s] | 18.53 | 53.50 | 58.24 |
| Increase of LST ST [%] | 0 | 189 | 214 |

Comparative Example 3

An SMMS spunmelt nonwoven web was produced from Ziegler-Natta polypropylene in a continuous production on a 4.5 m wide Reifenhäuser Reicofil 3 SMMS line. Each layer of S-layers had a weight of 9.5 g/m$^2$ and each of the M layers had a weight of 1.5 g/m$^2$, resulting in a thermally bonded SMMS nonwoven having a total weight per area of 22 g/m$^2$.

In each of the following five Examples the single layers of the SMMS sheet will be denoted as indicated in parentheses: S(1)M(2)M(3)S(4).

Example 6

A spunmelt nonwoven web was produced following the process described in Comparative Example 3, where the polymer forming Layer 4 contained 0.8% w/w of additive component, comprising at least 90% by weight of the additive component of glycerol tristearate, resulting in an average weight percentage of 0.3% w/w of additive component in the total web

Example 7

A spunmelt nonwowen web was produced as described in Example 1, where the polymer forming each of the Layers 1 and 4 contained 0.8% w/w of additive, as above, resulting in an average weight percentage of 0.7% w/w of active ingredient in the total web.

Example 8

A spunmelt nonwoven web was produced as described in Example 6, where the polymer forming each of the Layers 1 and 4 contained 1.6% w/w of additive component, as above, resulting in an average weight percentage of 1.4% w/w of active ingredient in the total web.

Example 9

A web was produced as described in Example 1, where the polymer forming each of the layers 1 and 4 contained 2.4% w/w of additive component as above, resulting in an average weight percentage of 2.1% w/w of active ingredient in the total web.

Example 10

A web was produced according to Example 1, where the polymer forming each of the Layers 1, 2 and 4 contained 2.4% w/w of additive component as above, resulting in an average weight percentage of 2.2% w/w of active ingredient in the total web.

The contents of active ingredient of Comparative Example 3 as well as of Examples 6 through 10 are summarized in Table 6.

TABLE 6

| | Lay-up [g] | | | | Configuration |
|---|---|---|---|---|---|
| | S | M | M | S | SMMS |
| | 9.5 | 1.5 | 1.5 | 9.5 | 22 g |
| Example | Active ingredient per layer [%] | | | | Average [%] |
| C3 | 0 | 0 | 0 | 0 | 0.0 |
| 6 | 0 | 0 | 0 | 0.8 | 0.3 |
| 7 | 0.8 | 0 | 0 | 0.8 | 0.7 |
| 8 | 1.6 | 0 | 0 | 1.6 | 1.4 |
| 9 | 2.4 | 0 | 0 | 2.4 | 2.1 |
| 10 | 2.4 | 2.4 | 0 | 2.4 | 2.2 |

The Alcohol Repellency was measured, with the test set out above, for Comparative Example 3 as well as Examples 6 to 10 and the results are shown in Table 7

TABLE 7

| | Alcohol Repellency | | | | | |
|---|---|---|---|---|---|---|
| Example | C3 | 6 | 7 | 8 | 9 | 10 |
| | 3 | 4 | 5 | 5 | 5 | 6 |
| | 3 | 4 | 6 | 5 | 5 | 6 |
| | 3 | 4 | 5 | 5 | 6 | 6 |
| | 3 | 4 | 5 | 6 | 5 | 6 |
| | 3 | 4 | 6 | 5 | 6 | 6 |
| Average | 3 | 4 | 5 | 5 | 5 | 6 |

The low surface tension strike through (32 mJ/m$^2$) was measured, as set out above, for Comparative Example 3 as well as Examples 6 to 10 and the results are shown in Table 8.

TABLE 8

| Example | C3 | 6 | 7 | 8 | 9 | 10 |
|---|---|---|---|---|---|---|
| Strike through (32 mJ/m$^2$) [s] | 16.04 | 24.72 | 26.25 | 29.41 | 36.51 | 44.14 |
| Increase of LST ST [%] | 0 | 54 | 64 | 83 | 128 | 175 |

The Handle-O-Meter CD-Stiffness as well as the Handle-O-Meter MD-Stiffness were measured for Comparative Example 3 as well as for Examples 6 to 10 and the respective values are given in Tables 9 and 10.

TABLE 9

| | Handle-o-Meter CD-stiffness [g] | | | | | |
|---|---|---|---|---|---|---|
| Example | C3 | 6 | 7 | 8 | 9 | 10 |
| | 7.9 | 6.6 | 6.0 | 5.0 | 5.1 | 4.9 |
| | 8.7 | 5.9 | 5.0 | 5.5 | 4.4 | 4.8 |
| | 7.3 | 6.0 | 5.4 | 5.0 | 4.9 | 5.1 |
| | 8.1 | 6.0 | 5.3 | 4.6 | 4.9 | 5.0 |
| | 5.9 | 6.1 | 4.4 | 5.3 | 5.1 | 4.0 |
| Average | 7.6 | 6.1 | 5.2 | 5.1 | 4.9 | 4.8 |
| Std dev | 1.1 | 0.3 | 0.6 | 0.3 | 0.3 | 0.4 |
| Min | 5.9 | 5.9 | 4.4 | 4.6 | 4.4 | 4.0 |
| Max | 8.7 | 6.6 | 6.0 | 5.5 | 5.1 | 5.1 |

TABLE 10

| | Handle-o-Meter MD-stiffness [g] | | | | | |
|---|---|---|---|---|---|---|
| Example | C3 | 6 | 7 | 8 | 9 | 10 |
| | 11.6 | 10.4 | 9 | 10.1 | 9.9 | 8.7 |
| | 13.9 | 11.0 | 8.8 | 9.9 | 8 | 9.6 |
| | 12.3 | 10.9 | 10 | 7.9 | 8.7 | 8.8 |
| | 13.3 | 10.7 | 10 | 9.3 | 9.1 | 8.2 |
| | 11.9 | 10.8 | 10.8 | 8.6 | 8.5 | 8.0 |
| Average | 12.6 | 10.8 | 9.7 | 9.2 | 8.8 | 8.7 |
| Std dev | 1.0 | 0.2 | 0.8 | 0.9 | 0.7 | 0.6 |
| Min | 11.6 | 10.4 | 8.8 | 7.9 | 8.0 | 8.0 |
| Max | 13.9 | 11.0 | 10.8 | 10.1 | 9.9 | 9.6 |

Elastic Modulus

This test determines the elastic modulus, also referred to as "web modulus", which is defined by the slope of the force-strain curve, of a sample of a barrier component or of a nonwoven barrier material, as described herein, that is, however, free of additional elastic material(s).

Any electronic Tensile Tester can be used, provided it reports the elastic (web) modulus at given strains, and it is operating following the operating instruction manual, and the following procedure. A sample is removed from an absorbent article; the sample should be free of elastic material and free of any damage. For MD-testing: the sample size is chosen such that it is suitable for the camps or jaws of the tensile tester; for example, the tensile tester may have 51 mm long jaws and the sample may then be suitably cut to be 51 mm wide (CD) to fit the jaws (air activated jaws with flat face); the length of the sample (MD) is chosen such that it is sufficient to fit the jaws and to cover the distance between opposing jaws at the start of the test (gauge length), e.g., 50.0 mm, so, for example, 60 mm total. For CD-testing: a new sample is used and the opposite dimensions apply.

Other jaws or clamp or gauge lengths may be chosen and sample sizes may be adjusted accordingly.

The sample is conditioned for 24 hours at 23° C. and 50% humidity, prior to this test, which is subsequently performed under the same conditions.

The calliper of the sample is then tested according to EDANA 30.5-99 section 4.1 (method A).

The tensile tester is calibrated and the gauge length is set according to the sample size, e.g. 50.0 mm; the cross-head speed is set to be 500 mm/min; pre-load 0.1N; the jaw pressure is set such that the sample can be clamped without slipping, for example 410 kPa. The programme is set to calculate the slope of the stress-strain curve in N % strain using a linear regression on the point between 0.5% of the given strain, and it will calculate the elastic modulus in N/mm$^2$.

The testing is performed under the same conditions as above. The sample is inserted between vertically between the jaws, such that there is no slack; the test is then started.

The programme calculates the elastic modulus as (N/% strain)×(100% strain/web areas (mm$^2$)). The web area is the (calliper×CD width) for samples tested for MD elastic modulus; and (calliper×MD length) when tested for CD elastic modulus.

The test is repeated with further samples, to obtain an average elastic modulus in CD and an average elastic modulus in MD (average over 3).

Samples of the spunmelt nonwoven web of example 8 above and samples of comparative example 3 above were tested and the results are reported in Table 11.

TABLE 11

| | MD Elastic modulus | | | | | | | |
|---|---|---|---|---|---|---|---|---|
| Nonwoven: strain | | 1% | 2% | 3-7% | 4-9% | 12-15% | 12-17% | 15-17% | 17-20% |
| Comparative example 3 | (N/mm$^2$) | 13.48 | 13.33 | 24.27 | 18.56 | 8.70 | 8.24 | 7.57 | 6.68 |
| Example 8 | (N/mm$^2$) | 11.75 | 11.62 | 19.72 | 15.09 | 7.37 | 7.00 | 6.46 | 5.68 |
| | CD Elastic modulus | | | | | | | |
| nonwoven strain | | 1% | 2% | 3-7% | 4-9% | 12-15% | 12-17% | 15 17% | 17-20% |
| Comparative example 3 | (N/mm$^2$) | 4.44 | 3.92 | 8.14 | 6.59 | 4.00 | 3.86 | 3.63 | 3.32 |
| Example 8 | (N/mm$^2$) | 3.17 | 3.29 | 6.62 | 5.33 | 3.36 | 3.27 | 3.09 | 2.90 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent hygiene article comprising a barrier component configured to touch the skin of a wearer when the absorbent hygiene article is donned, the barrier component comprising a nonwoven barrier sheet, the nonwoven barrier sheet comprising a nonwoven web or nonwoven layer made of fibers, the fibers made from one or more thermoplastic polymers and an additive component comprising one or more fatty acid esters, wherein the additive component is present in centers of at least some of the fibers and on surfaces of the at least some of the fibers, and wherein the additive component is present at a higher concentration at the surfaces than in the centers.

2. The absorbent hygiene article as in claim 1, wherein the additive component is a melt additive component comprising one or more fatty acid esters of an alcohol with two or more functional hydroxyl groups, forming an ester bond with two or more fatty acids.

3. The absorbent hygiene article as in claim 2, wherein the fatty acid ester is a triglyceride ester.

4. The absorbent hygiene article as in claim 3, wherein the additive component comprises a triglyceride ester of stearic acid.

5. The absorbent hygiene article as in claim 1, wherein the thermoplastic polymers comprise isotactic thermoplastic polymers.

6. The absorbent hygiene article as in claim 5, wherein the isotactic thermoplastic polymers comprise polypropylene.

7. The absorbent hygiene article as in claim 1, wherein the thermoplastic polymers comprise polyolefins.

8. The absorbent hygiene article as in claim 7, wherein the fibers comprise at least 90% by weight of the thermoplastic polyolefin polymer and from 0.5% to 10% by weight of the additive component.

9. The absorbent hygiene article as in claim 1, wherein the nonwoven barrier sheet has pores of a largest pore size of less than 60 microns and a mean flow pore size of from 10 to 30 microns.

10. The absorbent hygiene article as in claim 1, wherein the nonwoven barrier sheet comprises a spunmelt nonwoven web comprising at least a spunbond layer with spunbond fibers, the spunbond fibers comprising the one or more thermoplastic polymers and the additive component.

11. The absorbent hygiene article as in claim 10, wherein the nonwoven barrier sheet comprises a spunmelt nonwoven spunbond-meltblown-meltblown-spunbond web with a Low Surface Tension Strike Through value of at least 20 seconds.

12. The absorbent hygiene article as in claim 10, wherein the nonwoven barrier sheet comprises a spunmelt nonwoven spunbond-meltblown-meltblown-meltblown-spunbond web with a Low Surface Tension Strike Through value of at least 40 seconds.

13. The absorbent hygiene article as in claim 1, wherein the barrier component comprises an elasticated portion formed from a portion of the nonwoven barrier sheet and one or more elastic materials.

14. The absorbent hygiene article as in claim 13, wherein the elasticated portion is patterned.

15. The absorbent hygiene article as in claim 1, wherein the barrier component comprises a skin care composition that is a separate material from the additive component.

16. The absorbent hygiene article as in claim 1, wherein the barrier component comprises a pigment or an ink composition comprising a pigment.

17. An absorbent hygiene article comprising a barrier component, wherein the barrier component is positioned adjacent to the skin of a wearer when the absorbent hygiene article is donned, the barrier component comprising a nonwoven barrier sheet, the nonwoven barrier sheet comprising a nonwoven web or nonwoven layer made of fibers, the fibers made from one or more thermoplastic polymers and an additive component comprising one or more fatty acid esters, wherein the nonwoven barrier sheet comprises a spunmelt nonwoven web, wherein the spunmelt nonwoven web comprises at least a spunbond layer with spunbond fibers, wherein the spunbond fibers comprise the one or more thermoplastic polymers and the additive component, wherein the nonwoven barrier sheet comprises a spunmelt nonwoven spunbond-meltblown-meltblown-spunbond web with a Low Surface Tension Strike Through value of at least 20 seconds.

18. An absorbent hygiene article comprising a barrier component, wherein the barrier component comprises a cuff of the absorbent hygiene article, the barrier component comprising a nonwoven barrier sheet, the nonwoven barrier sheet comprising a nonwoven web or nonwoven layer made of fibers, the fibers formed from a composition comprising one or more thermoplastic polymers and an additive component, wherein the additive component is a melt additive comprising one or more fatty acid esters of an alcohol with two or more functional hydroxyl groups, forming an ester bond with two or more fatty acids, wherein the fatty acid ester comprises a triglyceride ester, and wherein the triglyceride ester comprises steric acid.

19. An absorbent hygiene article comprising a barrier component configured to touch the skin of a wearer when the absorbent hygiene article is donned, the barrier component comprising a nonwoven barrier sheet, the nonwoven barrier sheet comprising a nonwoven web or nonwoven layer made of fibers, the fibers comprising one or more thermoplastic polymers and an additive component comprising one or more fatty acid esters, wherein the nonwoven barrier sheet has pores of a largest pore size of less than 60 microns and a mean flow pore size of from 10 to 30 microns.

20. An absorbent hygiene article comprising a barrier component configured to touch the skin of a wearer when the absorbent hygiene article is donned, the barrier component comprising a nonwoven barrier sheet, the nonwoven barrier sheet comprising a nonwoven web or nonwoven layer made of fibers, the fibers comprising one or more thermoplastic polymers and an additive component comprising one or more fatty acid esters, wherein the barrier component comprises a pigment or an ink composition comprising a pigment, and wherein the nonwoven barrier sheet has pores of a largest pore size of less than 60 microns and a mean flow pore size of from 10 to 30 microns.

21. The absorbent hygiene article as in claim 17, wherein the Low Surface Tension Strike Through value is at least 40 seconds.

22. The absorbent hygiene article as in claim 19, wherein the fatty acid ester comprises stearic acid.

23. The absorbent hygiene article as in claim 19, wherein the nonwoven barrier sheet comprises a spunmelt nonwoven web comprising at least a spunbond layer with spunbond fibers, and wherein the spunbond fibers comprise the one or more thermoplastic polymers and the additive component.

24. The absorbent hygiene article as in claim 23, wherein the nonwoven barrier sheet comprises a spunmelt nonwoven spunbond-meltblown-meltblown-spunbond web with a Low Surface Tension Strike Through value of at least 20 seconds or at least 40 seconds.

25. The absorbent hygiene article as in claim 19, wherein the barrier component comprises an elasticated portion formed from a portion of the nonwoven barrier sheet and one or more elastic materials, and wherein the elasticated portion is patterned.

26. The absorbent hygiene article as in claim 19, wherein the barrier component comprises a skin care composition that is a separate material from the additive component.

27. The absorbent hygiene article as in claim 19, wherein the barrier component comprises a pigment or an ink composition comprising a pigment.

28. The absorbent hygiene article as in claim 19, wherein the additive component is present in centers of at least some of the fibers and on surfaces of the at least some of the fibers.

29. The absorbent hygiene article as in claim 19, wherein the additive component is present at a higher concentration at the surfaces than in the centers.

* * * * *